United States Patent
Yoshimine

(10) Patent No.: US 7,291,106 B2
(45) Date of Patent: Nov. 6, 2007

(54) DIAGNOSTIC SYSTEM AND PORTABLE TELEPHONE DEVICE

(76) Inventor: Takashi Yoshimine, 5-3-107, Minami-cho, Toda-shi, Saitama, 335-0025 (JP)

( * ) Notice: Subject to any disclaimer, the term of this patent is extended or adjusted under 35 U.S.C. 154(b) by 741 days.

(21) Appl. No.: 10/472,568

(22) PCT Filed: Jul. 31, 2002

(86) PCT No.: PCT/JP02/07820

§ 371 (c)(1),
(2), (4) Date: Sep. 25, 2003

(87) PCT Pub. No.: WO03/068062

PCT Pub. Date: Aug. 21, 2003

(65) Prior Publication Data

US 2004/0109571 A1    Jun. 10, 2004

(30) Foreign Application Priority Data

Feb. 18, 2002   (JP)   ............................. 2002-040028

(51) Int. Cl.
*A61B 5/00* (2006.01)
(52) U.S. Cl. .................... 600/301; 128/920; 381/67
(58) Field of Classification Search ................ 600/300, 600/301; 709/230, 240, 246; 382/133; 128/903–905, 128/920; 381/67
See application file for complete search history.

(56) References Cited

U.S. PATENT DOCUMENTS 5,987,519 A * 11/1999 Peifer et al. ................ 709/230
6,181,811 B1 * 1/2001 Kuan et al. .................. 382/133
6,206,829 B1 * 3/2001 Iliff ............................. 600/300

FOREIGN PATENT DOCUMENTS

| | | |
|---|---|---|
| JP | 59-184400 A1 | 10/1984 |
| JP | 2000-033077 A1 | 2/2000 |
| JP | 2000-139856 A1 | 5/2000 |
| JP | 2000-232964 A1 | 8/2000 |
| JP | 2001-309916 A1 | 11/2001 |
| JP | 2001-353160 A1 | 12/2001 |
| JP | 2002-015068 A1 | 1/2002 |
| WO | WO-00/32088 A1 | 6/2000 |

* cited by examiner

Primary Examiner—Max F. Hindenburg
Assistant Examiner—Sharick Naqi
(74) Attorney, Agent, or Firm—Rader, Fishman & Grauer PLLC

(57) ABSTRACT

A patient registers his audible sound when he is in good health. When he is not feeling well, and even when he is in good health, he may contact regularly with a medical institution. Once he pronounces words to his mobile phone, the audible sound will be stored in a storing portion for storing audible sound information of the patient and will be processed by a computer that gives diagnosis to the patient and the patient will be informed of the diagnosis through a public line.

5 Claims, 11 Drawing Sheets

DIAGNOSTIC SYSTEM AND PORTABLE TELEPHONE DEVICE

TECHNICAL FIELD

This invention relates to, for example, a diagnosing system causing a medical institution located at a place distant from a patient to examine a health condition of the patient. The invention is also related to a mobile phone used in the diagnosing system.

BACKGROUND ART

Recently, a diagnosing system rendering a patient to receive a "distant medical care" by doctors, experts and the like while staying at home is gradually being constructed. The "distant medical care" is, for example, transmitting information on the body of the patient such as electrocardiogram data and audible sound of body to a medical institution through the internet and the like, and the doctor analyses the information and makes a diagnosis.

Especially the unexamined patent application publication No. 2000-033077 discloses a system in that the patient uses apparatuses such as an electrocardiograph and a stethoscope and transmits the information obtained with the devices to the medical institutions. In addition, the publication also discloses a system using so called "videophone system", that is, the patient takes a picture of himself and transmits the image-information such as his complexion to the medical institution.

However, with the medical system explained above, in a case when the patient is to transmit the electro-cardiogram data, for example, the apparatuses that patient needs to be equipped with will be large and cumbersome. In addition, the patient needs to have knowledge of experts on an electro-cardiograph. Furthermore, the image-information mentioned above merely takes pictures such as the complexion of the patient and his overall image, therefore, it is difficult to comprehend condition of the patient in concrete and precise way.

Moreover, in recent years, quite a lot of people are health conscious, not only among the people with illness but also among healthy people and so called "health fad" is not considered to decline in future.

DISCLOSURE OF INVENTION

Considering the present circumstances mentioned above, the object of the present invention is to provide a system and a mobile phone of simple structure used in the system for the purpose of making diagnosis. The system renders the patient to receive appropriate diagnosis while staying at home. The system also renders a person with no health problems to receive a medical checkup casually.

To accomplish the above-described objects, according to the first aspect of the present invention, the present invention is comprised of means for causing a medical institution located at a place distant from a patient to receive an audible sound information actually pronounced by the patient and means for making a first diagnosis on a health condition of the patient corresponding to the received audible sound information and transmitting the diagnosis to the patient.

According to the present invention, the audible sound information actually pronounced by the patient is transmitted to, for example, a specialized agencies such as the medical institution mentioned above, through a public line such as the inter-net. The medical institution examines the patient corresponding to the audible sound information. The diagnosis made by the medical institution is then transmitted to the patient and enabling the patient to receive a precise diagnosis casually. Here, the medical institution is also able to make a diagnosis on whether a person is ill or not by comparing the audible sound information of the patient with the audible sound information stored when the patient is in good health. With this process, both the efficiency and speed in making diagnosis can be improved.

According to a second aspect of the present invention, the present invention is comprised of storing means storing audible sound information of the patient when the patient is in good health, audible sound information transmitting means for transmitting the audible sound information actually pronounced by the patient to a medical institution located at a place distant from the patient, audible sound information receiving means for receiving the transmitted audible sound information and means for making a first diagnosis on a health condition of the patient by comparing the received audible sound information of the patient with the stored information and transmitting the first diagnosis to the patient.

According to the present invention, the audible sound information of the patient when the patient is in good health is stored as a data beforehand. The audible sound information actually pronounced by the patient is transmitted to, for example, a specialized agencies such as the medical institutions mentioned above through the public line such as the inter-net. The medical institution gives diagnosis to the patient by comparing the audible sound information of the patient with the audible sound information stored when the patient is in good health. The diagnosis made by the medical institution is then transmitted to the patient, enabling the patient to receive a precise diagnosis casually.

In this case, means for transmitting the audible sound information is preferably a mobile phone carried by the patient. Like this example, with the use of the mobile phone that is a commonly owned commodity by many people, people could receive medical examination casually. In addition, by making the medical institution transmit the diagnosis to the mobile phone of the patient, the patient could check the diagnosis displayed, for example, on the liquid crystal display.

According to one embodiment of the present invention, the audible sound information transmitted to the medical institution is the audible sound information of the patient used in a normal conversation. Here, "the normal conversation" means a conversation takes place in daily life over the mobile phone and not the conversation with the medical institutions mentioned above. By transmitting the audible sound information naturally pronounced by the patient in everyday conversation, the patient is able to receive the medical examination casually without being too much conscious of receiving the examination.

According to one embodiment of the present invention, one of the audible sound information transmitting means and the audible sound information receiving means transmits and receives a predetermined words that are selected from the audible sound information actually pronounced by the patient. By having words that are used very often such as "hello" as predetermined words, more precise and accurate diagnosis can be made. Moreover, according to the present invention, diagnosis are made corresponding to the everyday conversation of the patients, therefore, problems as to infringement of privacy may arise. However, by picking up the predetermined words that are generally used as in the present invention, such problems could be avoided.

According to yet another embodiment of the present invention, one of the audible sound information transmitting means and the audible sound information receiving means transmits and receives the audible sound information for a predetermined time period beginning from when the patient starts communicating. The problems such as infringement of privacy can be avoided as in the case mentioned above by using conversation made for the predetermined period of time, for example, for the first few seconds from the beginning thereof, for making diagnosis.

According to one embodiment of the present invention, means for obtaining a magnified image of a saliva spattered as the patient speaks and image transmitting means for transmitting the magnified image of the saliva to the medical institution. The medical institution receives the transmitted image of the saliva and makes the first diagnosis by examining the patient corresponding to the transmitted image of the saliva and the audible sound information, then transmits the first diagnosis to the patient. As in this case, when speaking over the mobile phone, a bit of saliva should be spattered around the sound pick-up portion of the mobile phone. Therefore by providing the magnifying means such as a CCD near the sound pick-up portion thereof, the diagnosis based on the microscopic image of the saliva should become possible. With this embodiment, in addition to the diagnosis based on the audible sound information of the patient, diagnosis based on the saliva is made possible, rendering the patient to receive more detailed diagnosis casually. Moreover, by transmitting the diagnosis to the mobile phone owned by the patient, the patient is able to obtain his diagnosis easily.

According to another embodiment, the present invention further comprising, means for making a second diagnosis of the patient different from the first diagnosis when a disparity is found between the first diagnosis and the second diagnosis by comparing the first diagnosis with the second diagnosis. For example, by performing a medical examination with higher technology than the first diagnosis, the patient is able to know of the deceases more precisely.

According to yet another embodiment of the present invention, the means for making the second diagnosis has a diagnosing apparatus having an image pick-up means for picking up an image information and a stethoscope for picking up a sound information and that the image pick-up means and the stethoscope are integrally connected, means for transmitting the picked-up sound information and the image information obtained from the diagnosing apparatus to the medical institution and means for causing the medical institution make the second diagnosis of the patient corresponding to the picked-up sound information and the picked-up image information by the diagnosing apparatus and transmitting the second diagnosis to the patient. With this embodiment, for example, in the same time as auscultating audible sound of body such as heartbeat, sound of blood stream, the condition of the skin and the complexion of the patient can also be examined casually.

In addition, the stethoscope has a sound pick-up portion and an image pick-up portion being disposed inside the sound pick-up portion, that picks up an image of the patient as touching the patient. By looking into, for example, condition of the skin and the complexion of the patient, blood and body fluid and the like, the patient is able to receive a more advanced diagnosis. In such case, by using the CCD, the CMOS and the like the image can be processed digitally enabling the medical institution to receive clear image information.

According to one embodiment of the present invention, the mobile phone has a speaker and a vibration detecting sensor, the sensor is disposed near the speaker, and the sensor detects a vibration caused on a face of the patient as the patient communicates and outputting a signal corresponding to the detected vibration, and the medical institution examines the patient corresponding to the outputted signal from the vibration detecting sensor, then transmits the first diagnosis. The patient places the part of the mobile phone that functions as a speaker on his/her ear when using thereof, and the vibration of the patient's voice is transmitted to the mobile phone through his/her face. Then, by comparing, for example, the audible sound information of the patient with the audible sound information caused by the vibration and analyzing thereof, the medical institution is able to examine abnormality in the shape of the cheek bone and the jaw bone of the patient.

A mobile phone of the present invention has a means for obtaining a magnified image of human saliva.

According to the present invention, when speaking over the mobile phone, a bit of saliva may be assumed to spatter around the sound pick up portion of the mobile phone. Therefore by providing the magnifying means such as the CCD near the sound pick-up portion, the diagnosis based on the microscopic image of the saliva should become available. In that case, the magnifying means is preferably provided with a lens system introducing the picked-up image of the saliva to the CCD. With this embodiment, a micro image of the saliva could be obtained and a more advanced diagnosis will become available.

Characteristics and benefits of the present invention will become more obvious with referencing the explanation of the attached "drawings" and "embodiments".

BEST MODE OF CARRYING OUT THE INVENTION

Preferred embodiments of the present invention will be explained below with reference to the drawings.

Figure 1:
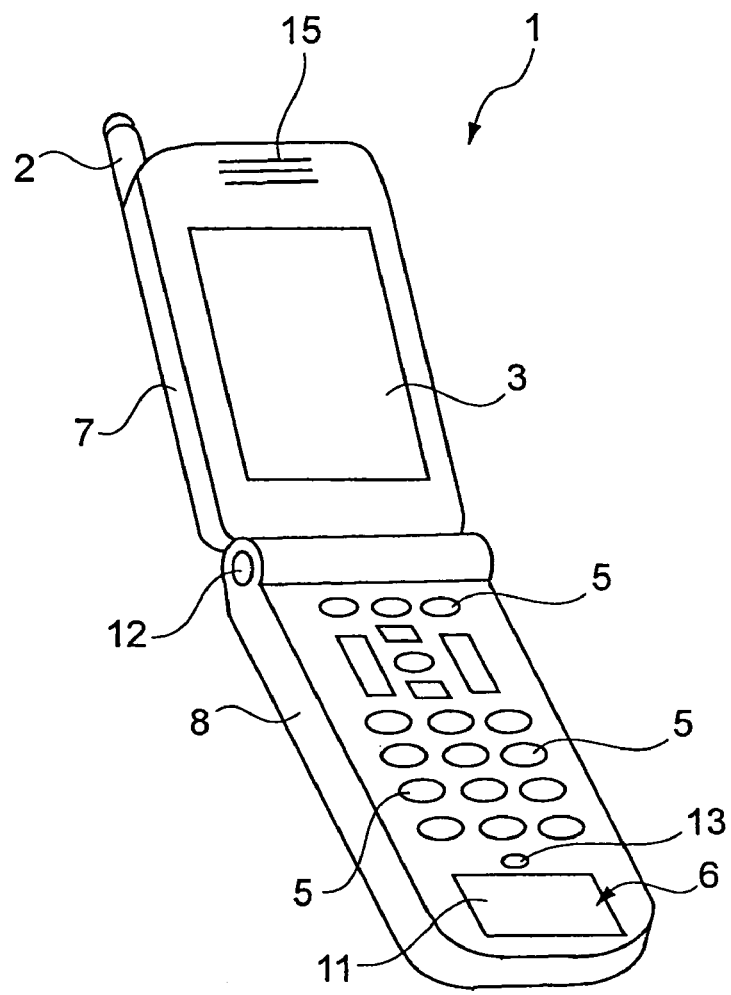
FIG. 1 is a perspective view of the mobile phone relating to an embodiment of the present invention.

FIG. 1 is a perspective view of the mobile phone relating to an embodiment of the present invention. The mobile phone 1 is a mobile phone generally used and, for example, a main body of a display 7 and a main body of a manipulating portion 8 are engaged with each other by a axis 12, thus the mobile phone 1 is so-called a "folding type" mobile phone. For example, the main body of the display portion 7 is provided with apparatuses such as, a display 3 comprised of a liquid crystal display, an antenna 2, and a speaker 15. The main body of the manipulating portion 8 is provided with a manipulating button 5, an opening portion 9 for picking-up sound and a magnifying apparatus 6.

Figure 2:
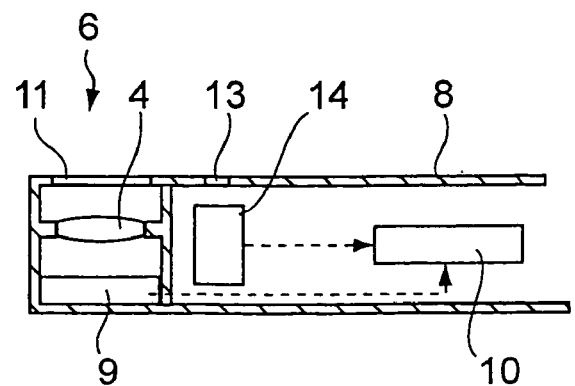
FIG. 2 is a partial sectional view of the SOD system shown in FIG. 1.

FIG. 2 is a sectional view showing the main body of the manipulating portion 8 mentioned above. The magnifying apparatus 6 has a structure using, for example, a transparent acryl plate 11 provided on the front side of the manipulating portion 8, a lens system 4 and a CCD 9 provided inside the main body of the manipulating portion 8. With this embodiment, an image of saliva adhered to the acryl plate 11 can be obtained as a digital image information. In addition, a microphone 14 for obtaining the audible sound information pronounced as the patient speaks is provided inside the manipulating portion 8. A control circuit 10 processes image information obtained from the CCD and the audible sound information obtained from the microphone 14. The control circuit 10 also integrally controls data input using the button, outputting data to the display 3 and the like.

Figure 3:
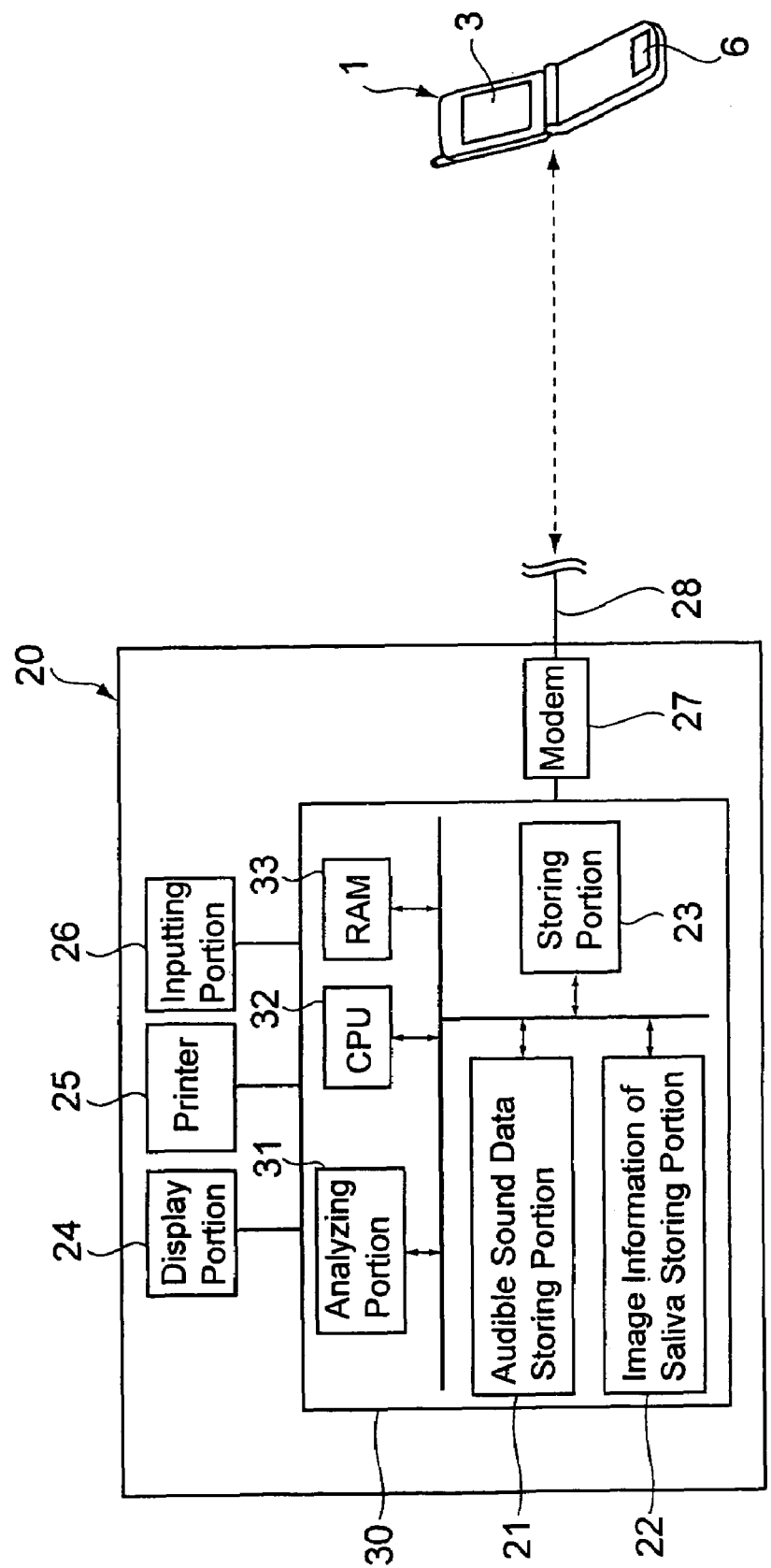
FIG. 3 is a configuration diagram showing a SOD system according to the first embodiment of the present invention.
Figure 4:
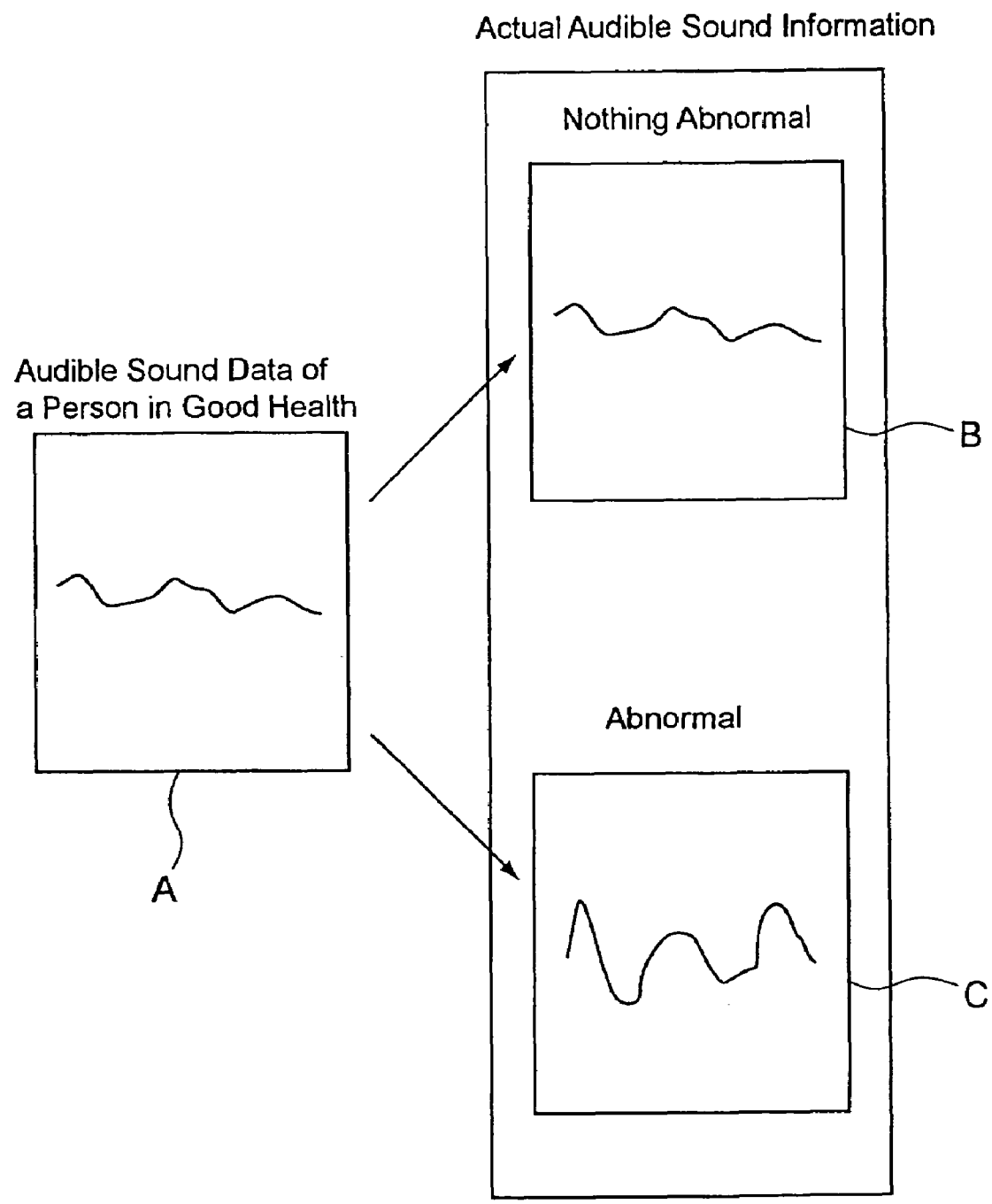
FIG. 4 is a diagram showing a waveform obtained as a result of comparison between the audible sound data when the patient is healthy and the audible sound information actually picked up by the patient.

FIG. 3 is a diagram showing a structure of a diagnosing system in relation to the first embodiment of the present invention using the mobile phone 1 shown in FIGS. 1 and 2. In the diagnosing system, for example, a medical institution 20 such as hospitals, clinics and the like, are equipped with a computer 30, having a display portion 24, an outputting portion 25 such as a printer, an inputting portion 26 such as a keyboard and a modem 27. The computer 30 has a storing portion 21 for storing an audible sound data of a person in good health, a storing portion 23 for storing an audible sound information of a patient, a storing portion for storing an image information of saliva 22, an analyzing portion 31, a CPU 32 and a RAM 33.

In the storing portion 21, the audible sound of a patient when he/she is in good health is stored previously. In this case, the patient himself may send his audible sound when he/she is in good health to the medical institution 20 using the aforesaid mobile phone 1. The storing portion 23 for storing the audible sound information of a patient stores the audible sound actually pronounced by the patient using the mobile phone 1. The storing portion 22 for storing image information of the saliva stores image information of the saliva adhered to the acryl plate 11 as the patient speaks through the mobile phone 1. In the analyzing portion 31 the audible sound information stored in the storing portion 23 and the audible sound data stored in the storing portion 21 are compared and analyzed to diagnose a disease. Also, a diagnosis is given based on the image information of the saliva stored in the storing portion 22.

In such diagnosing system, the patient previously registers his audible sound when he/she is in good health. When he is not feeling well, and even regularly when he is in good health, he may contact with the medical institution 20 and pronounce words to his mobile phone 1. In this manner, the audible sound is processed by the computer 30 that gives diagnosis to the patient and the diagnosis is transmitted to the patient through the public line 28. In such case, phrases like "nothing abnormal" or "the name of the disease is: . . . " may be displayed as a diagnosis on the display 3 of the mobile phone 1 of the patient. By displaying on the mobile phone 1, the patient is able to know his/her diagnosis easily.

A concrete diagnosing method of the medical institution 20, is, for example, the audible sound data of a person in good health shows a wave form (in an intensity distribution of the audible sound frequency, for example) represented as A and the audible sound information of the patient picked up by the mobile phone has a wave form represented as B, a phrase "no abnormality is found" is transmitted to the patient and when the audible sound information has a wave form represented as C, a phrase "abnormality is found" is transmitted to the patient.

In addition, through the microscopic image examination of the saliva, abnormality in oral cavity, salivary gland, nose and ears, throat, lung, tooth and the like can be examined. Especially, accurate image examination of the saliva becomes possible by combining thereof with the audible sound information.

In this case, the medical institution 20 may pick up and examine only the predetermined words of the audible sound of the patient. The predetermined words are words that the patient often uses in a conversation through a telephone, for example, words like "hello" or phrases beginning with "This is . . . ", the words that the patient uses when he/she tells his/her name to start the conversation.

Alternatively, words designated by a doctors and the like stationed at the medical institution 20. Like this example, by giving diagnosis to the patient using frequently used words, more precise and accurate diagnosis can be made. In other words, as they are the words that are used frequently, minute differences can be detected in comparison with the state in good health. Moreover, using words designated by the medical institution 20, the examination can be performed with words that are necessary for giving highly precise diagnosis in the most efficient way.

Furthermore, as for the saliva, image information thereof may be transmitted automatically from the mobile phone 1 on a regular basis, for example, once or several times per month, once a day, or may be upon request of the patient.

In addition, the diagnosis for the patient in this embodiment may be made fully automatically using a computer or may be intervened by a doctor when necessary.

According to the diagnosing system in the embodiment explained as above, the patient is able to receive a precise diagnosis with ease. The system also renders a person with no health problems to receive a physical checkup casually.

Figure 5:
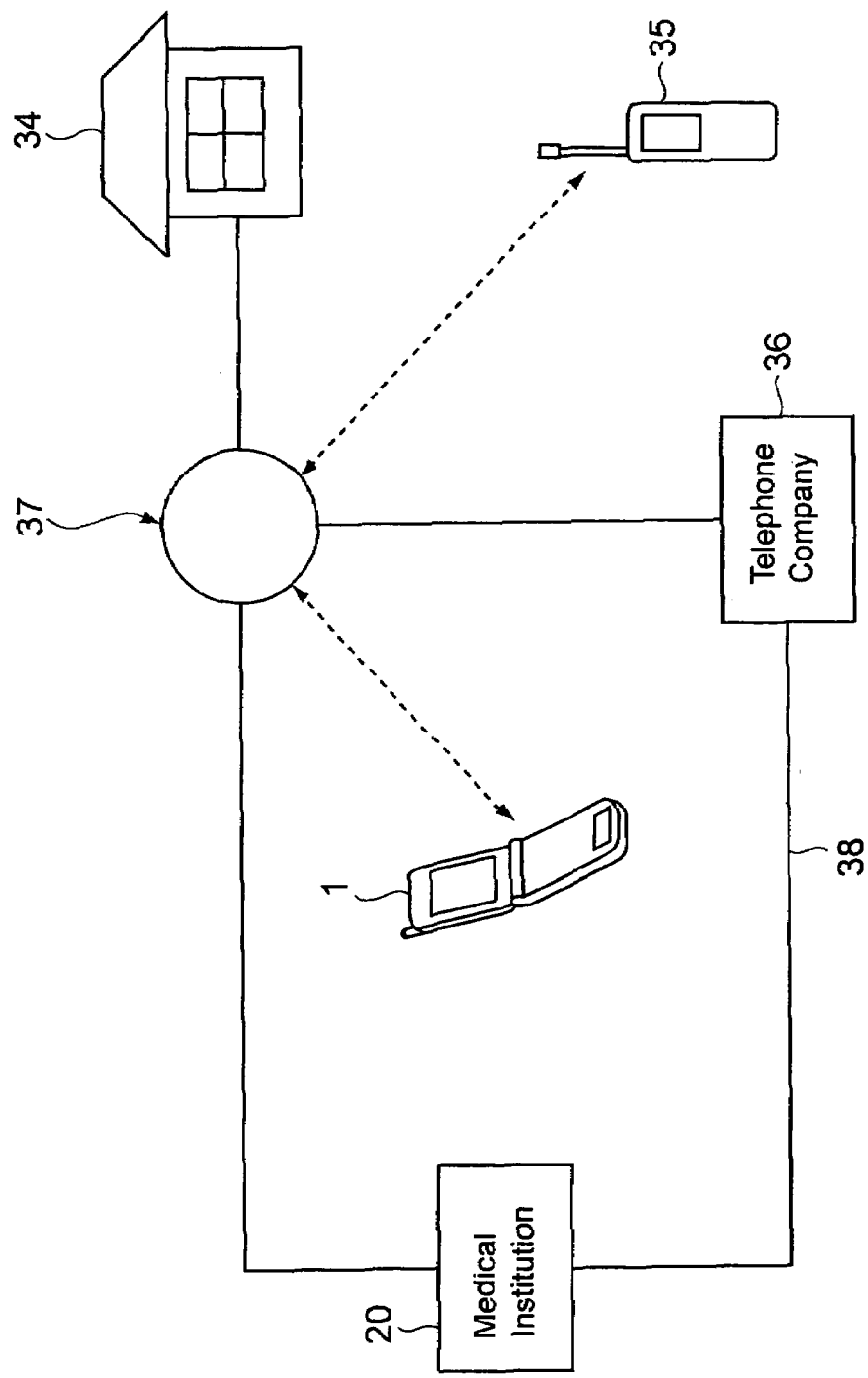
FIG. 5 is a diagram showing a configuration of the public line in detail as shown in FIG. 3.

FIG. 5 is a diagram showing the public line 28 shown in FIG. 3 in detail. According to the diagram, the mobile phone 1 is able to communicate with the medical institution 20, a telephone company 36, an indoor telephone set 34, and other mobile phones 35 and the like through the public line 37. The public line of this kind is used so that when the patient having the mobile phone 1 calls, for example, the indoor telephone set 34, or other mobile phone 35 owned by an acquaintance or the like, at least one of the aforesaid audible sound information or the image information of saliva is transmitted to the medical institution 20. In this case, the medical institution 20 needs to reach some kinds of an agreement with the telephone company 36. With this process, even if the patient does not telephone directly to the medical institution 20, the audible sound information and the image information of saliva of the patient can be transmitted to the medical institution 20 out of normal conversation. Hereby, the patient can receive diagnosis automatically without paying attention thereto.

In this case, considering the privacy of the patient, as mentioned above, the audible sound information of predetermined words, or alternatively, the first several seconds of the conversation may be transmitted to the medical institution. Additionally, in this case also the audible sound information or the image information of saliva may automatically be transmitted from the mobile phone 1 on regular basis, for example, once or several times per month, once a day, or upon request by the patient. Furthermore, a dedicated line 38 may be established between the telephone company 36 and the medical institution 20, transmitting information from the patient to the medical institution 20.

With such diagnosing system, anyone is able to continuously receive medical diagnosis from the time when he/she is in good health, which realizes early detection and prevention of diseases.

Figure 6:
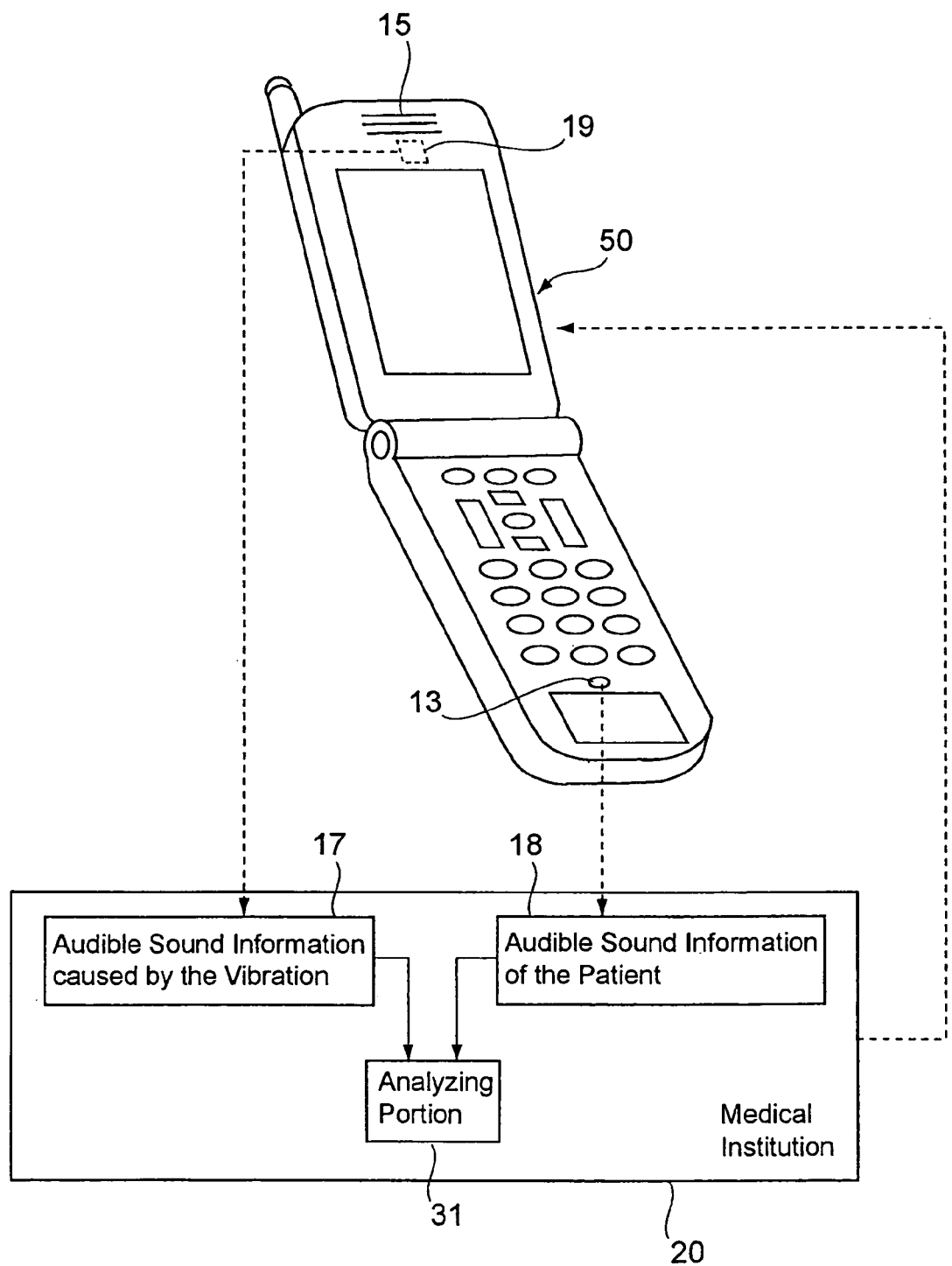
FIG. 6 is a perceptive view of the mobile phone relating to an embodiment of the present invention.

FIG. 6 is a perceptive view of the mobile phone in relation to another embodiment of the present invention. According to the present embodiment, a vibration sensor 19 is provided inside and, close to the speaker 15 of the aforesaid mobile phone 1. This is to detect the vibration transmitted to the face, for example, to the cheek of the patient caused when the patient is using the mobile phone 50 using the vibration sensor 19 provided in the speaker 15, digitize what is detected and transmit the data to the medical institution 20. In other words, the patient puts the speaker 15 on his/her ear when using the mobile phone 50, therefore, the vibration of the patient's voice will be transmitted to the mobile phone 50 through his/her face. A piezoelectric sensor can be used as the vibration sensor 19.

In such system, by comparing and analyzing the audible sound information of the patient 18 with the audible sound information 17 caused by the vibration using the analyzing portion 31 at the medical institution 20, the medical institution is able to examine abnormality in the shape of a cheek bone and a jaw bone of the patient.

Figure 7:
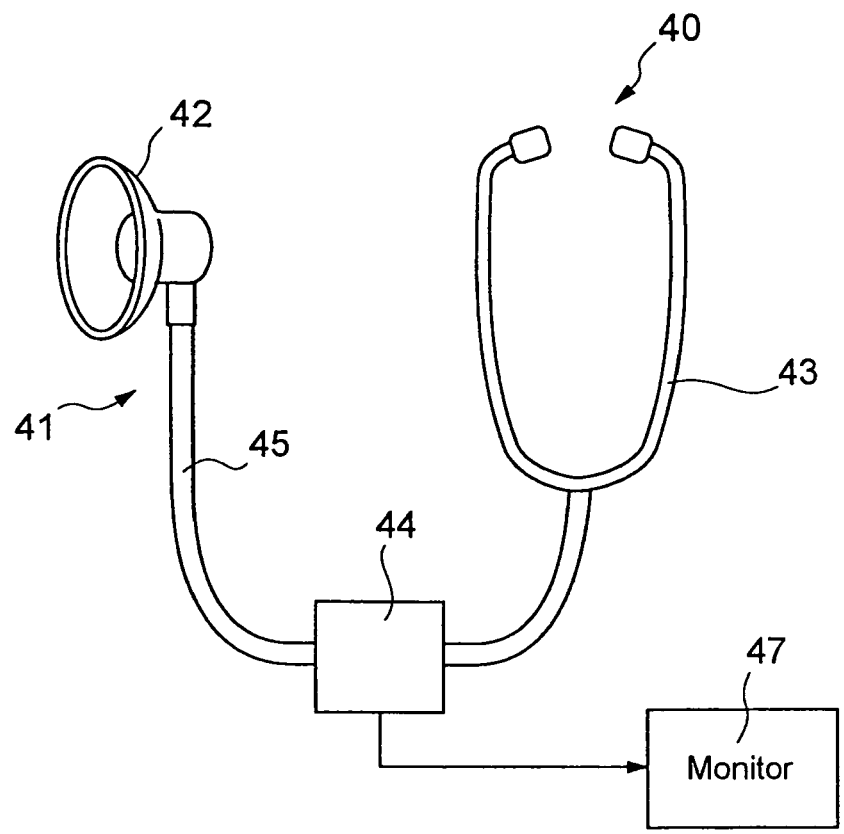
FIG. 7 is a perspective view of the diagnosing apparatus relating to an embodiment of the present invention.

FIG. 7 is a diagnosing apparatus relating to an embodiment of the present invention. A diagnosing apparatus 40 is comprised of a digital stethoscope 41, a signal transformer 44 provided in the middle of a cable 45 of the digital stethoscope and a monitor 47 is connected to the signal transducer 44.

Figure 8:
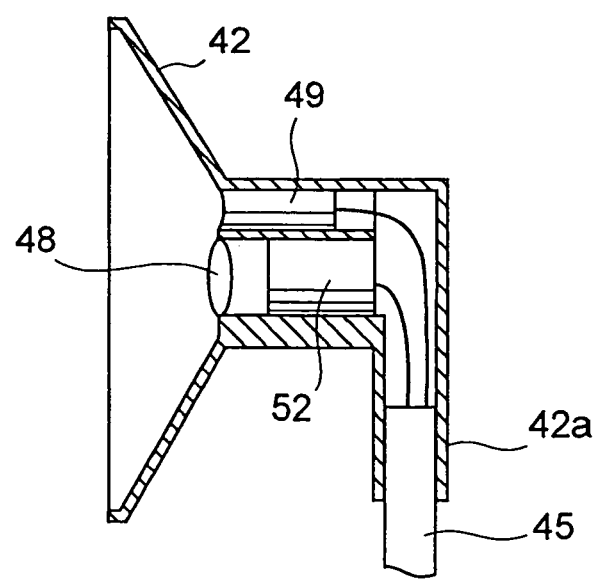
FIG. 8 is a partial sectional view of the diagnosing apparatus shown in FIG. 7.

As shown in FIG. 8, a microphone 49 to pick-up the audible sound of the body, a lens 48 and a camera 52 are provided inside the sound pick-up portion 42. The lens 48 is positioned so that images are focused on the camera 52. Magnified images can be formed inside the camera 52 using the lens 48. Inside a boss portion 42a of the sound pick-up portion 42, the cable 45 extended from the microphone 49 and the camera 52 are disposed. The camera 52 is comprised of, for example, a CCD and a CMOS that are possible to process digital image. In addition, as the number of picture element of CCD as for the camera 52 increases in the future, it will become possible to get a magnified image without the lens 48.

In the signal transformer 44, a processing circuit reproducing sound information from the microphone 49 in an auditory tube 43 of the digital stethoscope 41, a processing circuit visualizing image information, for example, to the monitor 47 with another amplifying circuit, a power supply circuit, a noise removal circuit, etc are provided therein. The processing circuit of the sound and the processing circuit of the image information are digitally processed. With this signal transformer 44, for example, image provided by the camera 52 are digitally processed and are made visible by the monitor 47. With this configuration, high sound quality and high image quality become possible to be reproduced.

According to the aforesaid structure of the diagnosing apparatus 40, the audible sound of the body such as heartbeat, sound of bloodstream can be examined with the stethoscope 41. In the same time, as the sound pick-up portion 42 touches the patient directly, the state of the skin, complexion, the internal state of the mouth (swell of the throat) and the like are possible to be examined easily through the lens 48, the camera 52, the monitor 47 etc.

In addition, taking the output image signal of the signal transformer 44 into a personal computer (not shown), the image can be stored easily.

Since the digital stethoscope 41 is used as a stethoscope in the diagnosing apparatus 40, for example, by having the auditory tube 43 of the digital stethoscope 41 attachable and detachable to and from the signal transformer 44, the auditory tube 43 can be detached from the signal transformer 44, and replaced with a speaker of a non-earphone type.

Figure 9:
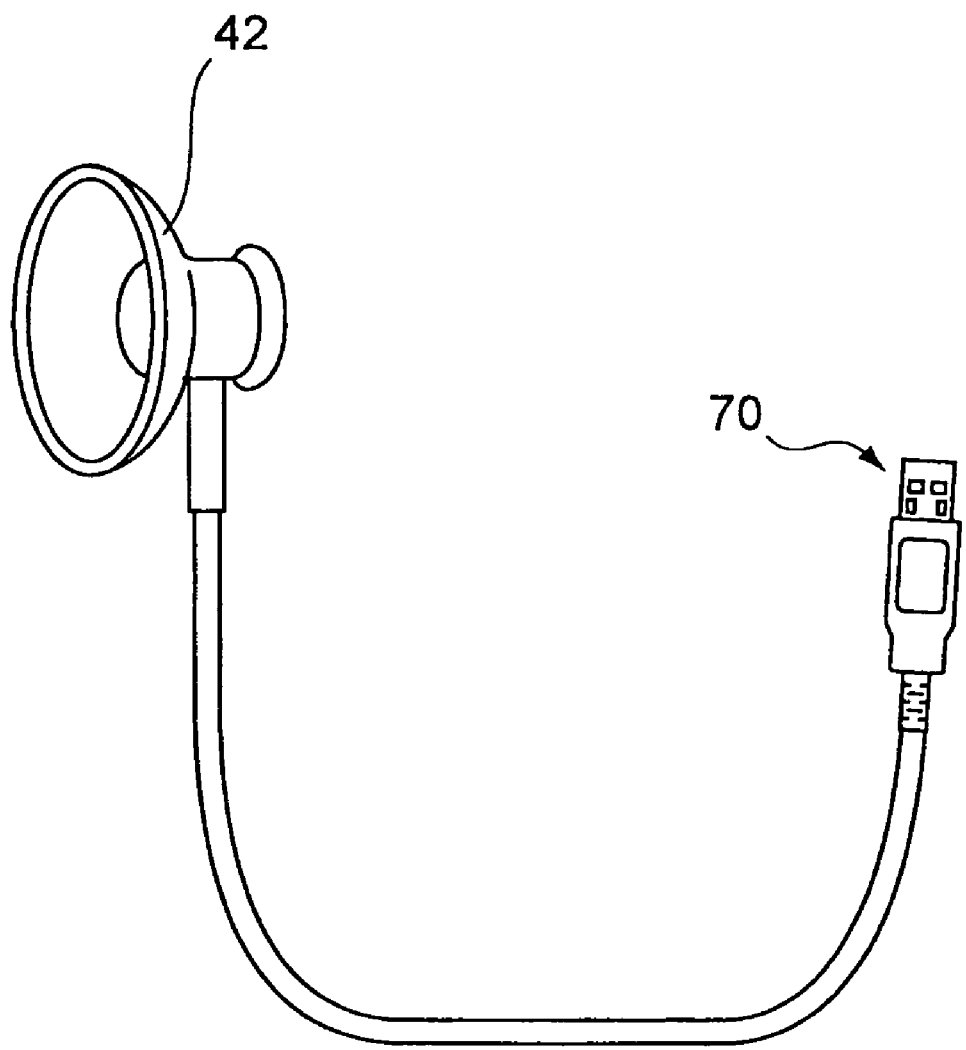
FIG. 9 is a perspective view of the diagnosing apparatus relating to another embodiment of the present invention.

Furthermore, as shown in FIG. 9, even without the transformer 44, the auditory tube 43 can be connected directly with the personal computer by changing thereof to an interface 70 having an USB connection.

Figure 10:
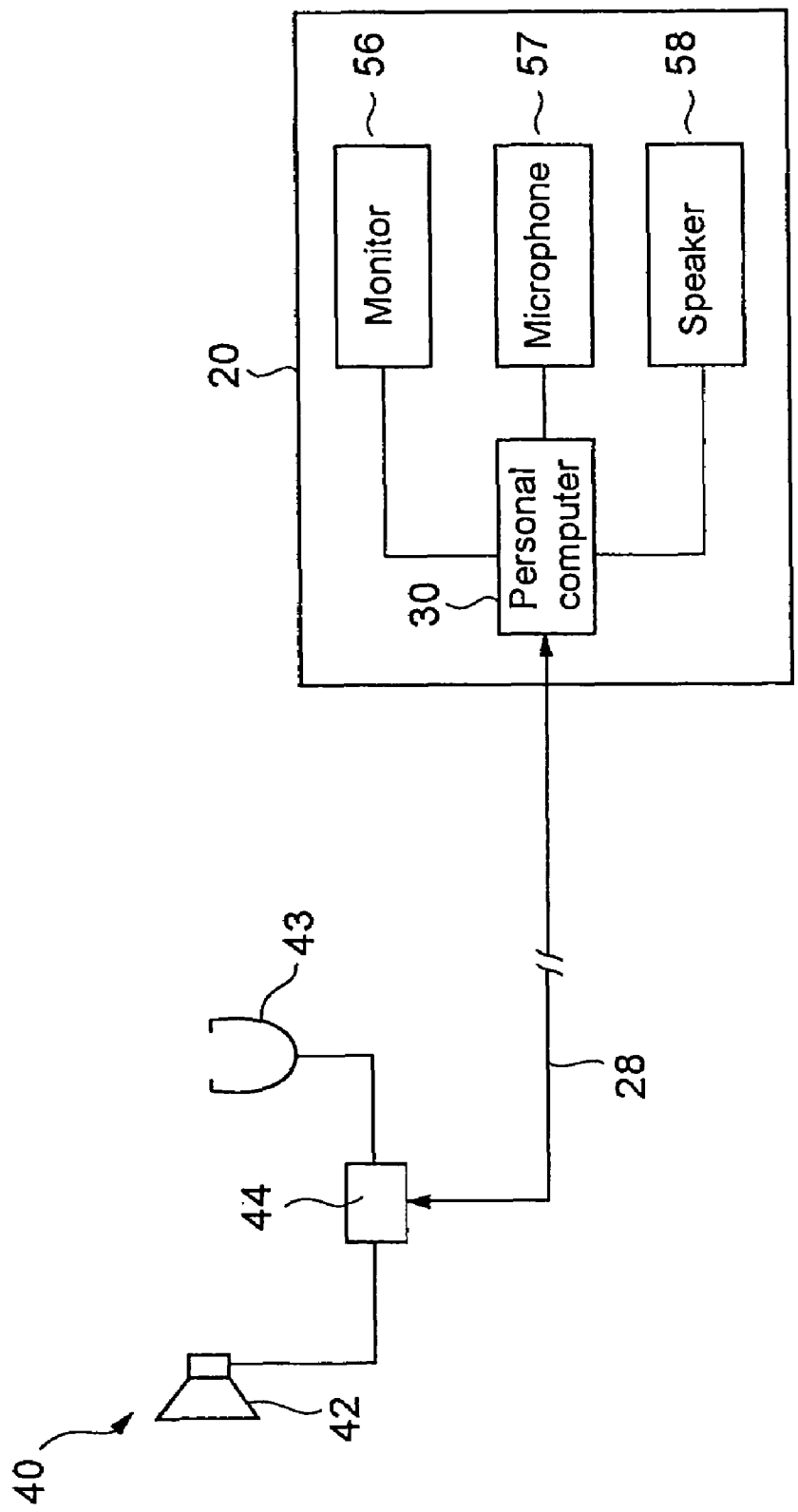
FIG. 10 is a diagram showing a configuration realizing the concept of the diagnosing system using the diagnosing apparatus.

FIG. 10 is an example showing a configuration realizing the concept of a diagnosing system using the above-explained diagnosing apparatus 40. The diagnosing apparatus 40 is connected, for example, with a personal computer 30 of the medical institution 20 via the communication means such as the public line 28. And the personal computer 30 is connected to each of the terminals like a monitor 56, microphone 57, a speaker 58 such as earphones. With this configuration, the audible sound information of the patient from the diagnosing apparatus 40 become reproducible through the earphone 58 and the image-information of the patient becomes reproducible through the monitor 56. Then, a doctors and the like examines the patient based on the information on the audible sound of the body and the image information. And the diagnosis can be transmitted to the patient through the communication means 28. Therefore, the patient can consult with a doctor at home.

Furthermore, in this case, it is possible for the patient to obtain audible sound of his/her body and the image by placing the sound pick-up portion 42 on himself/herself while hearing the doctor's voice with the auditory tube 43 of the stethoscope.

By practicing the diagnosing system of this kind, the following effects can be obtained.

As a first step, using the stethoscope of the present invention in a low magnification range, over-all observation of the body can be realized. In other words, for example, when the patient places the stethoscope on his/her body and the position where the stethoscope is placed is not the place that the doctor stationed at a distant place expects, the doctor can inform the patient that he/she is not touching the right place. Then, the patient should move the stethoscope placed on himself, slightly away from his body, so that the doctor could identify the position where the stethoscope was wrongly placed. The doctor, then could inform the patient the position he wishes him to touch.

Furthermore, the patient can turn the stethoscope to his/her own face and legs and arms so that general complexion and condition of his/her skin can be examined as well.

As a second step, by using the stethoscope of the present invention in, for example, a moderate magnification range, observation of the body parts becomes possible. For example, the doctors can obtain an image such as a condition of the part of the skin, a hairline, a hangnail or a thorn stuck on the tip of the nail. With this example, the patient is able to receive precise instructions from the doctor, by offering detailed body information compared to the first step mentioned as above.

Finally, as the third step, an observation of a patient in high microscopic range becomes possible by using the stethoscope of the present invention, for example, of high magnification. For example, the doctor is able to obtain images of blood, saliva, urine, feces, a part of skin and the like at a microscopic level and medical advice of even higher quality can be offered to the patient.

Figure 11:
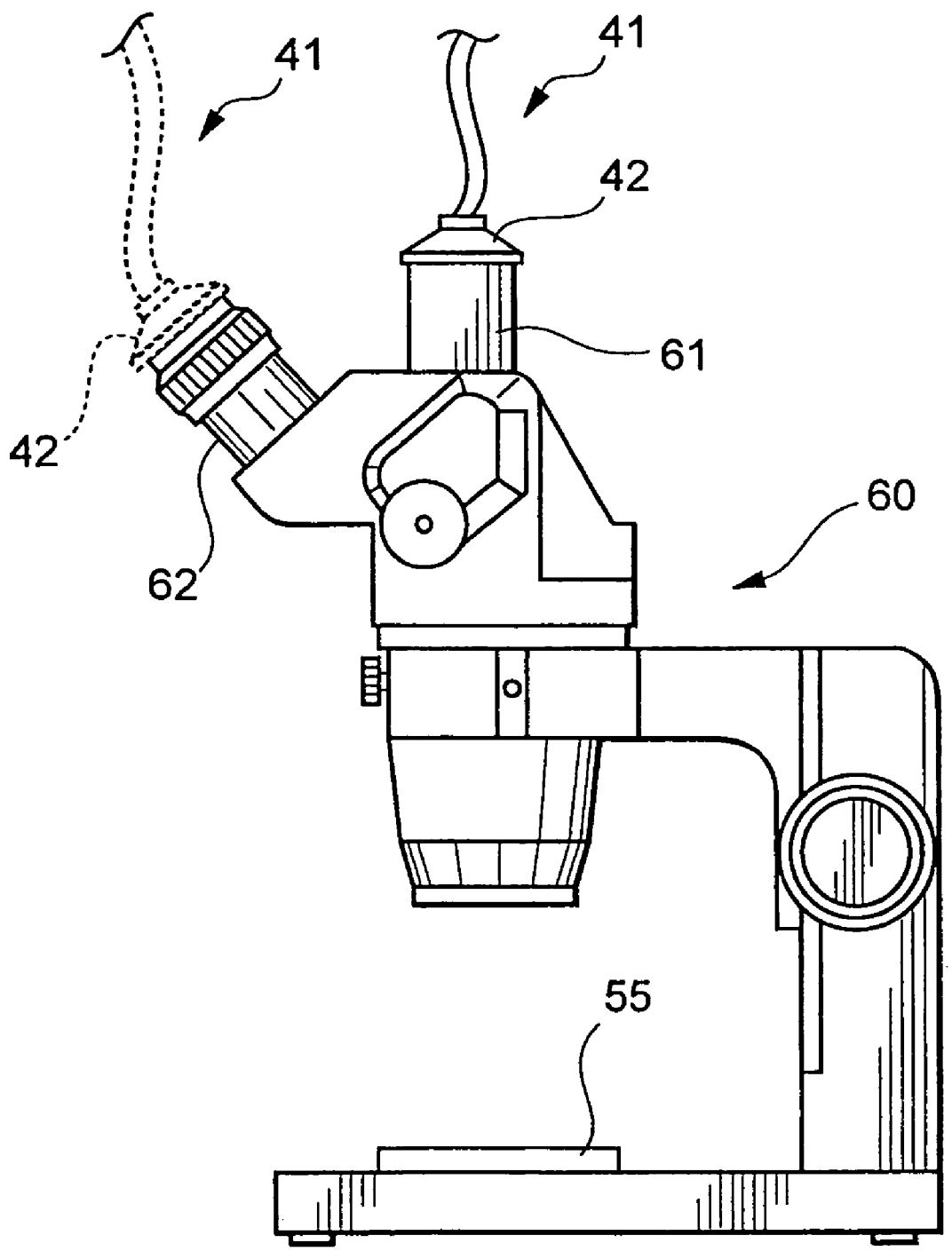
FIG. 11 is a diagram showing a configuration of the diagnosing apparatus in a case where the sound pick-up portion thereof is made attachable to the microscope.

As shown in FIG. 11, the microscope 60 can also be used for a diagnosis using images of high magnification. For example, in FIG. 11, the sound pick-up portion 42 of the digital stethoscope 41 is structured so that it can be mounted on the C-mount section 61 and the ocular portion 62 of the microscope 60. Concretely, a screw thread is provided at an end portion of the sound pick-up portion 42, either a screw groove or the screw thread is provided at the c-mount section 61 and an end portion of the ocular portion 62 a screw ditch or a screw thread is set up. Furthermore, when attached in such manner, observation with high magnification becomes possible by employing an optical design to allow an image obtained by the lens system of the microscope 60 to be formed in the camera 52 (FIG. 8), image sample 55 (an object to be examined that are placed on a slide prepared for a microscope) on the camera 52 (FIG. 8), which is provided inside the stethoscope 41. However, the number of pixels in CCD in the stethoscope 41 will sure to increase in future. For example, when the number of pixels increases by hundred millions, the observation can be performed with high magnification without using such stethoscope.

Nevertheless the microscope 60 is advantageous when examining an unsanitary object, for example, feces and the like since observing such objects directly with the stethoscope 41 is unsanitary.

Figure 12:
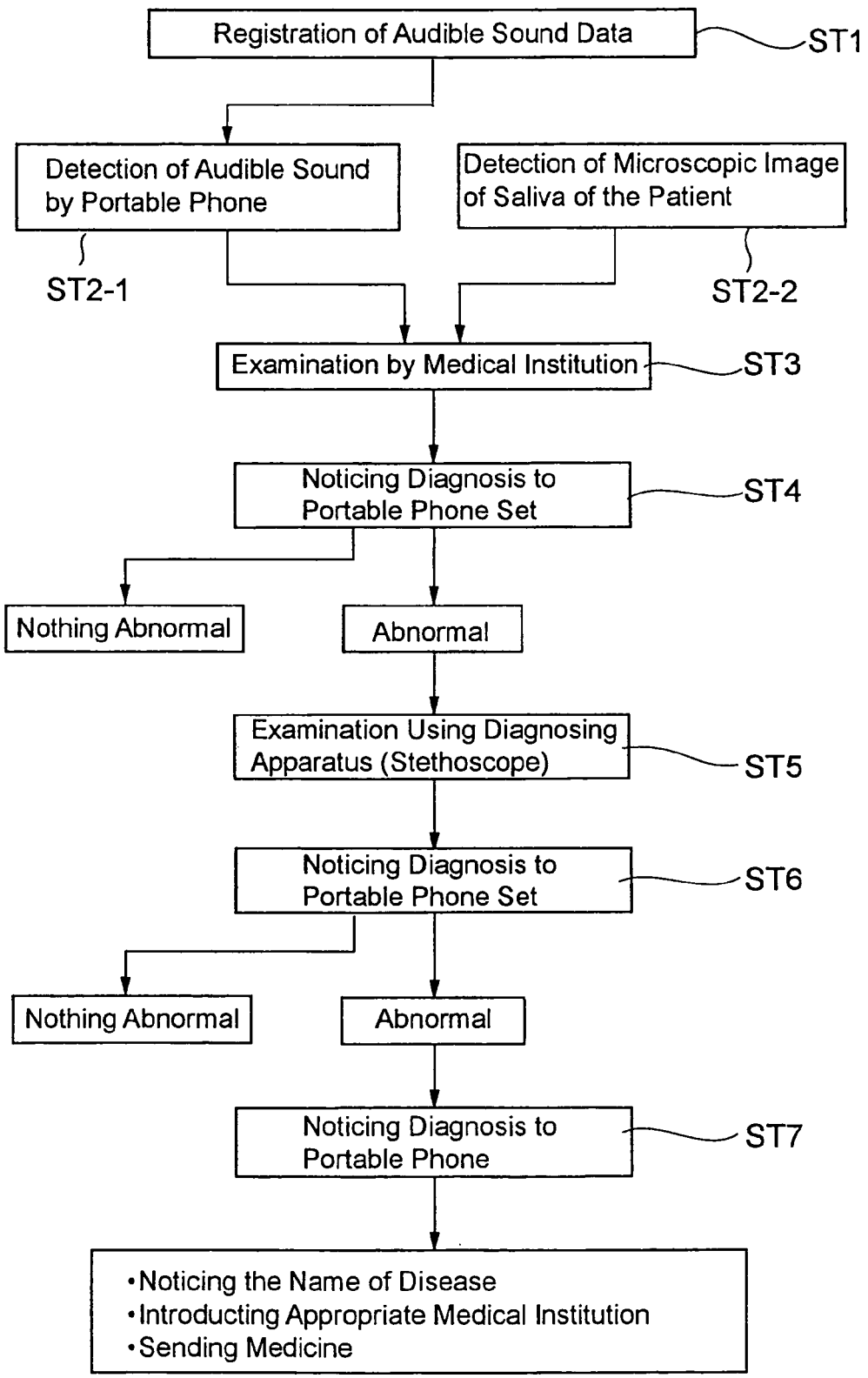
FIG. 12 is a flow chart showing the flow of a diagnosing system when the diagnosing system shown in FIG. 3 FIG. 5 and FIG. 10 are all combined together.
Figure 13A:
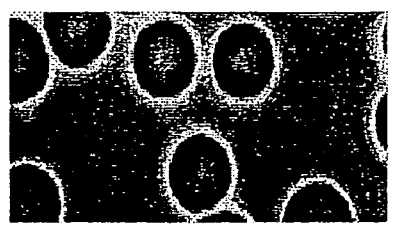
FIG. 13a through FIG. 13f are examples of photographs of a red blood cell taken through the microscope.
Figure 13B:
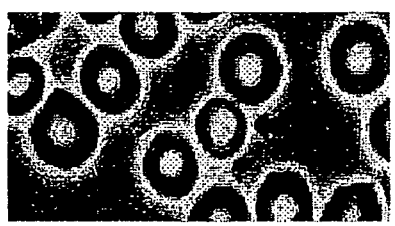
Figure 13C:
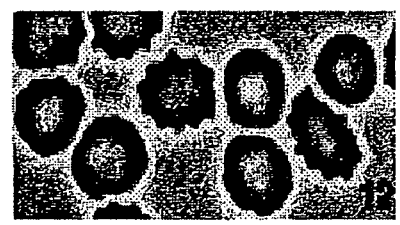
Figure 13D:
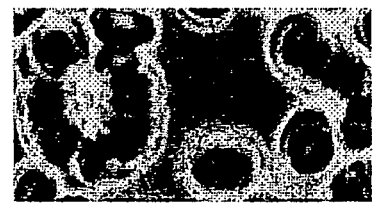
Figure 13E:
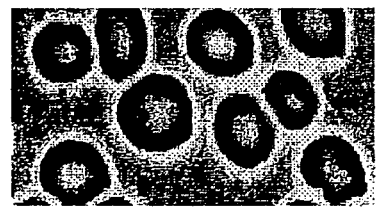
Figure 13F:
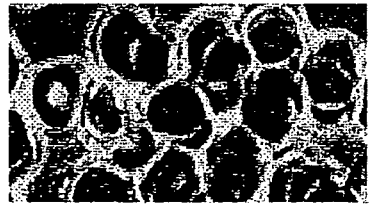

FIG. 12 is a flow chart explaining the flow of the diagnosing system when the system of the above-explained FIG. 3, FIG. 5 and FIG. 10 are combined together.

First, as described before, the audible sound when the patient is in good health will be registered (step 1), detecting audible sound of the patient with the mobile phone 1 (step 2-1), obtaining microscopic image of saliva of the patient (step 2-2), the medical institution 20 examines the patient (step 3), and the diagnosis is noticed to the mobile phone 1 (step 4).

When any abnormalities are found in the step 4, diagnosis by the diagnosing apparatus 40 (a digital stethoscope 41) (step 5) is performed. The diagnosis is transmitted to the mobile phone 1 as in the step 4 (step 7), and when any abnormality is found, actions such as notifying the name of the decease, introducing an appropriate medical institution, and sending medicine to the patient can be performed.

According to the present diagnosing system, a person with no outstanding health problems can have a casual medical check-up without even being conscious of being examined in the step 1 to the step 4. And once an abnormality is found, the patient is able to receive more advanced medical diagnosis in the steps after the step 5. With this embodiment, any person can continuously receive medical diagnosis from the time when he is in good health, and by performing more advanced medical diagnosis using the diagnosing apparatus 40 compared to the first diagnosis based on the audible sound and saliva, the patient can be informed of the precise name of the disease he/she has, therefore, contributes to early finding and prevention of deceases.

As above, having described the present invention with embodiments, the basis thereof is that the inventor strongly recommends individuals with sensory disorders to be the people to give diagnosis in the medical institution. Very often, a person with congenital sensory disorders, for example, a person with seeing disorder, has more developed senses among the five senses except for the visual sense, for example, more developed hearing sense than a person without any disorders. On the contrary, a person with a hearing disorder may have better seeing sense, than a person without any disorders. The inventor of the present invention is considering of offering places to work for the handicapped people in future, however, in the same time, he is considering that such people with sensory disorders should contribute to the society by themselves.

For example, a person with born seeing disorder could become better skilled professional of hearing sound through stethoscope than a doctor in future, once he/she is given such training from his/her childhood. The inventor of the present invention is contemplating of establishing a qualification such as "stethoscope diagnoser" and only a person who passed the examination can practice diagnosing patients using the present invention.

On the other hand, various diseases can also be found from a microscope image. At present, diagnosing a patient using blood, saliva, feces and tissues taken out from his/her body with a microscope is a common medical practice. It is not hard to imagine that people with hearing disorder could become a very skilled "diagnoser" once they given training on pathology judgment using a microscope from their childhood. Having people who passed the examination of a qualification like "microscopic image diagnoser" engage in working for the industry after the training, more advanced medical service becomes available.

In addition, sensory disorders of handicapped people do not have to be congenital but may be postnatal caused by accidents or diseases.

In the present medical science various diseases can be found from an audible sound of the body detected with a stethoscope. For example, various diseases of respiratory system can be recognized: low tone continuing sound is a sign of bronchial asthma or the like; high-pitch toned continuing sound is a sign of bronchial asthma, bronchial stenosis and the like; squawky sound is a sign of bronchiectasis; fine intermittent sound is a sign of pneumosclerosis, hypersensitivity pneumonitis, rheumatoid arthritis, heart failure (early phase) and the like; coarse intermittent sound is a sign of bronchiectasis, light pneumonia, lobar pneumonia, acute pulmonary edema and the like.

FIG. 13 is an example of microphotography of erythrocyte of a man. Examination like this type enables to know a health condition or, if a person has any deceases, condition of the deceases. The magnification of the microphotography is around 1000 times, and by using the stethoscope 41 of the present invention as shown in FIG. 11 and the system of the microscope 60, the patient is able to receive a blood examination at home. For reference, FIG. 13A shows erythrocyte of a healthy person; beautiful orbicular shape and a dent in the middle is a characteristic thereof. The picture FIG. 13B shows erythrocyte that is lacking in iron content, mineral and vitamin. The middle thereof becomes thin and, in some cases, may break to make a hole. FIG. 13C shows erythrocyte damaged with active oxygen. The damage is caused by pollution by chemicals and stress. FIG. 13D shows a state that viscosity of blood is increased and erythrocytes are sticking with each other. The cause thereof is excess nourishment and insufficient exercise. FIG. 13E shows a state that big and small erythrocyte co-exists that is caused by a lack of iron. Improvement in eating habits and exercise are required. FIG. 13F shows the state that viscosity of the blood increased even more, and the blood is eminently polluted. This could cause crucial diseases.

The present invention is not limited to an embodiment as described above, however, various kinds of modifications are possible.

For example, according to the forgoing embodiments, a folding type mobile phone is given as an example for the mobile phone 1, however, the mobile phone 1 is not limited to the folding type but a straight type may also be used. In addition, not only the mobile phones but also any means that are able to transmit the audible sound, including an orthodox type telephone set may be possible.

In addition, a temperature sensor, detecting the temperature of the saliva may be provided inside the mobile phone 1 of the forgoing embodiment, and the information on the temperature may also be transmitted to the medical institution 20.

Furthermore, when diagnosing the audible sound of the actual patient by the mobile phone 1, the medical institution 20 may send a reply message telling fortune of the day with words and/or cartoons to the mobile phone 1, based on the audible sound information.

In addition, the embodiments described above, uses "an open bell type" sound pick up portion 42 for the digital stethoscope 41, however, the embodiment is not limited to this type but also a "diaphragm type" may be used in order to collect only a sound of a predetermined frequency. In such case, it is possible to use, for example, a glass epoxy resin as the diaphragm so that the image information by the camera 52 can be obtained.

In addition, an illumination mechanism may be provided inside the sound pick-up portion 46 of the stethoscope 41 in the diagnosing apparatus of each of the aforesaid embodiment.

INDUSTRIAL APPLICABILITY

As explained above, according to the present invention, the patient is able to receive appropriate diagnosis while staying at home. The system also renders a person with no health problems to receive a physical checkup casually.

The invention claimed is:

1. A diagnosing system diagnosing a patient to communicate with a computer of a medical institution through a public line, comprising:

a stethoscope having a sound pick-up portion picking up a sound information and an image pick-up device picking up image information of the patient which is disposed inside the sound pick-up portion;

a signal transformer processing the sound information and the image information digitally, being connected with the computer, and transmitting the processed sound and image information digitally through the public line;

wherein the computer has:

receiving means for receiving the transmitted sound information and image information transmitted by the signal transformer; and first transmitting means for transmitting diagnosis information obtained from the medical institution based on the received sound information and image information by the receiving means.

2. The diagnosing system as set forth in claim 1, further comprising:

audible sound information transmitting means for transmitting audible sound information actually pronounced by the patient to the computer;

wherein the computer has:

storing means for storing the audible sound information of the patient obtained when the patient is in good health, as first audible sound information;

audible sound information receiving means for receiving the transmitted audible sound information;

analyzing means for comparing second audible sound information of the patient with the first audible sound information stored in the storing means and obtaining an audible sound-diagnosis information; and second transmitting means for transmitting the obtained audible sound-diagnosis information to the patient.

3. The diagnosing system as set forth in claim 2, wherein the audible sound information transmitting means is a mobile phone carried by the patient.

4. The diagnosing system as set forth in claim 1, wherein the image pick-up device is a charge coupled device (CCD) or a complementary metal oxide semiconductor (CMOS) device.

5. The diagnosing system as set forth in claim 1, further comprising:

an USB interface capable of outputting at least one of the sound information picked up by the sound pick-up portion and the image information picked-up by the image pick-up device.

* * * * *